(12) United States Patent
Jeong et al.

(10) Patent No.: US 12,011,336 B2
(45) Date of Patent: Jun. 18, 2024

(54) TOMOGRAPHY CONVERGENCE-TYPE ORAL SCANNER

(71) Applicants: HUVITZ CO., LTD., Anyang-si (KR); OSSVIS CO., LTD., Anyang-si (KR)

(72) Inventors: Hyo Sang Jeong, Anyang-si (KR); Su Min Han, Anyang-si (KR); Weon Joon Lee, Anyang-si (KR)

(73) Assignees: HUVITS CO., LTD., Anyang-si (KR); OSSVIS CO., LTD., Anyang-si (KR)

( * ) Notice: Subject to any disclaimer, the term of this patent is extended or adjusted under 35 U.S.C. 154(b) by 289 days.

(21) Appl. No.: 17/533,299

(22) Filed: Nov. 23, 2021

(65) Prior Publication Data
US 2022/0183799 A1    Jun. 16, 2022

(30) Foreign Application Priority Data
Dec. 15, 2020   (KR) .......................... 10-2020-0175365

(51) Int. Cl.
*A61C 9/00*    (2006.01)
*A61B 5/00*    (2006.01)
(Continued)

(52) U.S. Cl.
CPC .......... *A61C 9/0053* (2013.01); *A61B 5/0066* (2013.01); *A61B 5/0088* (2013.01); *G01B 9/02015* (2013.01); *G01B 9/02091* (2013.01)

(58) Field of Classification Search
None
See application file for complete search history.

(56) References Cited

U.S. PATENT DOCUMENTS

| | | | |
|---|---|---|---|
| 2008/0062429 A1 | 3/2008 | Liang et al. | |
| 2008/0118886 A1* | 5/2008 | Liang | A61B 5/0088 |
| | | | 433/29 |
| 2020/0288981 A1 | 9/2020 | Li et al. | |

FOREIGN PATENT DOCUMENTS

| | | | |
|---|---|---|---|
| EP | 2060227 A1 | 5/2009 | |
| KR | 10-2014-0107803 A | 9/2014 | |

(Continued)

OTHER PUBLICATIONS

KR20180032723A machine translation (Year: 2018).*
(Continued)

*Primary Examiner* — Jason M Ip
*Assistant Examiner* — Renee C Langhals
(74) *Attorney, Agent, or Firm* — United One Law Group LLC; Kongsik Kim; Jhongwoo Peck

(57) ABSTRACT

A tomography convergence-type oral scanner includes an oral scanning unit comprising a projector including a first light source for generating visible light, and a camera for generating image data by receiving the visible light reflected from a tooth; an optical tomography scanning unit comprising an OCT body including a second light source that has a different wavelength from the first light source and generates a measurement light incident on the tooth, a beam splitter for splitting the measurement light into a reference light and a measurement light, a reference mirror that reflects the reference light, and a photodetector for detecting an interference light, and an OCT scan probe including a collimator for converting the measurement light into a parallel light and a MEMS mirror for reflecting the converted parallel light; and a dichroic mirror for transmitting the visible light and reflecting the parallel light, thereby irradiating a tooth to be measured.

3 Claims, 3 Drawing Sheets

(51) Int. Cl.
*G01B 9/02* (2022.01)
*G01B 9/02015* (2022.01)
*G01B 9/02091* (2022.01)

(56) References Cited

FOREIGN PATENT DOCUMENTS

| KR | 10-1449168 B1 | 10/2014 |
| KR | 10-2018-0032723 A | 4/2018 |
| KR | 20180032723 A * | 4/2018 |
| KR | 10-2088951 B1 | 4/2020 |
| WO | 2008/063605 A2 | 5/2008 |
| WO | 2017/176300 A1 | 10/2017 |
| WO | 2019/002616 A1 | 1/2019 |
| WO | 2019/005055 A1 | 1/2019 |

OTHER PUBLICATIONS

European Search Report for EP 21212712.0 dated May 10, 2022.
Hsieh et al., "Dental Optical Coherence Tomography," Sensors 2013, 13, 8928-8949.
Son et al., "A Comparison Study of Marginal and Internal Fit Assessment Methods for Fixed Dental Prostheses," J. Clin. Med. Aug. 2019, 785.
Chen et al., "Quantifying dental biofilm growth using cross-polarization optical coherence tomography," Letters in Applied Microbiology 2012, 54, 537-542.
Le et al. "A noninvasive imaging and measurement using optical coherence tomography angiography for the assessment of gingiva: An in vivo study," Journal of Biophotonics Aug. 2018.

* cited by examiner

TOMOGRAPHY CONVERGENCE-TYPE ORAL SCANNER

CROSS-REFERENCE TO RELATED APPLICATION

This application claims priority to Korean Patent Application No. 10-2020-0175365 filed on Dec. 15, 2020, which is incorporated herein by reference in its entirety.

TECHNICAL FIELD

The present invention relates to a tomography convergence-type oral scanner, and more particularly, to a tomography convergence-type oral scanner that provides optical tomography images of the shape of a tooth surface and the inside of a tooth.

RELATED ART

In general, the conditions of intraoral teeth and tissues are checked by taking impressions of the teeth of a patient in dental clinics or the like, and based on this, it is an important clinical process that is the basis for establishing a diagnosis and treatment plan for a patient or producing an accurate prosthesis.

In general, conventionally, a two-dimensional transmission image of an intraoral tissue structure obtained by inserting a film in the shape of a sheet or a digital sensor into the oral cavity and then irradiating radiation such as X-rays from the outside of the oral cavity is used to identify the intraoral teeth and tissue structures, but errors such as distortion may occur as a two-dimensional transmission image projects and displays a three-dimensional structure onto a two-dimensional plane, clinical problems may be caused since the patient is exposed to radiation, and an economic burden and complexities at the stage of implementation are brought about.

Recently, in order to acquire three-dimensional information on the intraoral tissue structure, a dental oral scanner system that implements a three-dimensional modeling image of an intraoral tissue structure with measurement light such as a laser is widely used. A typical dental oral scanner system may include an oral scanner held and used by a user for scanning and photographing intraoral tissue structures, and a PC that is connected to the oral scanner by wire and generates scan and photographing results of the oral scanner into a 3D modeling image.

FIG. 1 is a diagram showing an oral scanner used in the prior art, and the oral scanner includes a projector 12 including a light source that irradiates the tooth s and a camera 14 including an image sensor to which the light irradiated to the tooth s is transmitted and that can obtain a surface image of the tooth s, as shown in FIG. 1 below. Specifically, the oral scanner may drive a light source (e.g., a light source in the visible light range) of an internal illumination to output light, then illuminate the inside of the oral cavity through the light irradiated to the outside along an optical path, and acquire surface shape data of the intraoral tooth as the light reflected from the inside of the oral cavity reaches the camera 14 including the image sensor of the oral scanner along the optical path again. At this time, the two-dimensional image detected by the camera 14 may be converted into a three-dimensional image by using triangulation.

In the case of using a conventional oral scanner, as there is a problem that an accurate condition and lesion of a tooth cannot be identified by taking an intraoral image only once, there is a hassle of having to take images several times. In addition, an oral scanner alone cannot determine the exact depth and location in the oral region, and in particular, the reality is that since there is no tooth depth information in diseases such as periodontal diseases such as periodontitis and subgingival (gum) margin acquisition, dental caries, cracks, etc., and thus it appears overlapping or is difficult to distinguish, it is difficult for doctors to make an accurate diagnosis.

Accordingly, there is a need to develop a device capable of measuring the external surface shape of a tooth and the internal tomography image of the tooth in the oral cavity.

SUMMARY

Therefore, it is an object of the present invention to provide a tomography convergence-type oral scanner capable of scanning the surface formation of a tooth and the internal shape of a tooth by combining an optical tomography scanner that can image the inside of a tooth with an oral scanner that aims to take an impression of a patient and acquire the surface shape of a tooth.

It is another object of the present invention to provide a tomography convergence-type oral scanner capable of non-invasively checking periodontal diseases such as periodontitis, dental caries, cracks, biofilms, and the like, by providing an optical tomography image of the inside of the tooth in addition to the shape of the tooth surface.

In order to achieve the objects above, the present invention provides a tomography convergence-type oral scanner comprising: an oral scanning unit comprising a projector including a first light source for generating visible light, and a camera for generating image data by receiving the visible light reflected from a tooth after the visible light generated from the light source is incident on the tooth; an optical tomography scanning unit comprising an OCT body including a second light source that has a different wavelength from the first light source and generates a measurement light incident on the tooth, a beam splitter for splitting the measurement light into a reference light and a measurement light, a reference mirror that reflects the reference light, and a photodetector for detecting an interference light generated by superposition of a signal light generated by reflection of the measurement light by the tooth and the reference light reflected by the reference mirror, and an OCT scan probe including a collimator for converting the measurement light divided by the beam splitter into a parallel light and a MEMS mirror for reflecting the converted parallel light; and a dichroic mirror for transmitting the visible light generated by the oral scanning unit and reflecting the parallel light reflected by the MEMS mirror of the optical tomography scanning unit, thereby irradiating a tooth to be measured.

In the tomography convergence-type oral scanner in accordance with the present invention, it is possible to scan the surface formation of a tooth and the internal shape of a tooth by combining an optical tomography scanner that can image the inside of a tooth with an oral scanner that aims to take an impression of a patient and acquire the surface shape of a tooth, and thus, it is possible to non-invasively check subgingival margin acquisition, dental caries, cracks, biofilm, periodontitis, or the like.

DETAILED DESCRIPTION

Figure 1:
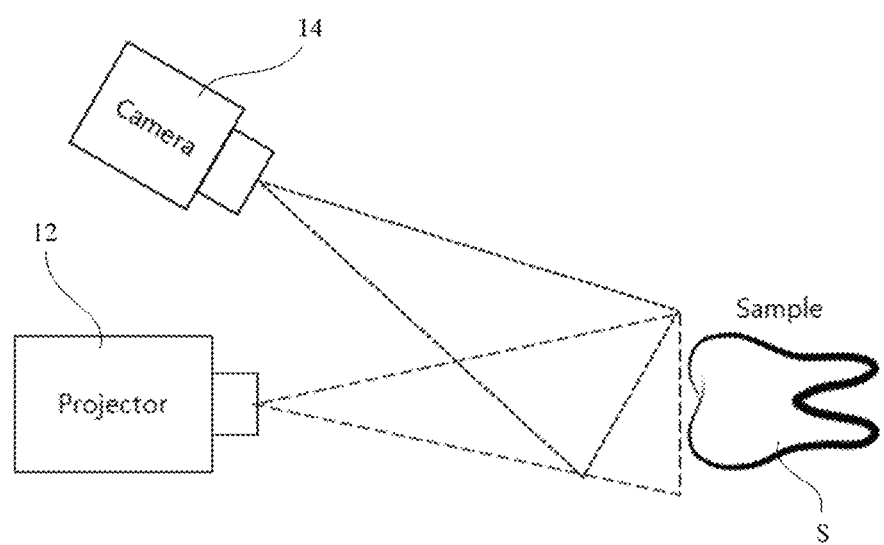
FIG. 1 is a diagram showing an oral scanner in accordance with the prior art.

Hereinafter, the present invention will be described in detail with reference to the accompanying drawings. In the accompanying drawings, the components performing the same or similar functions as in the prior art are assigned the same reference numerals.

Figure 2:
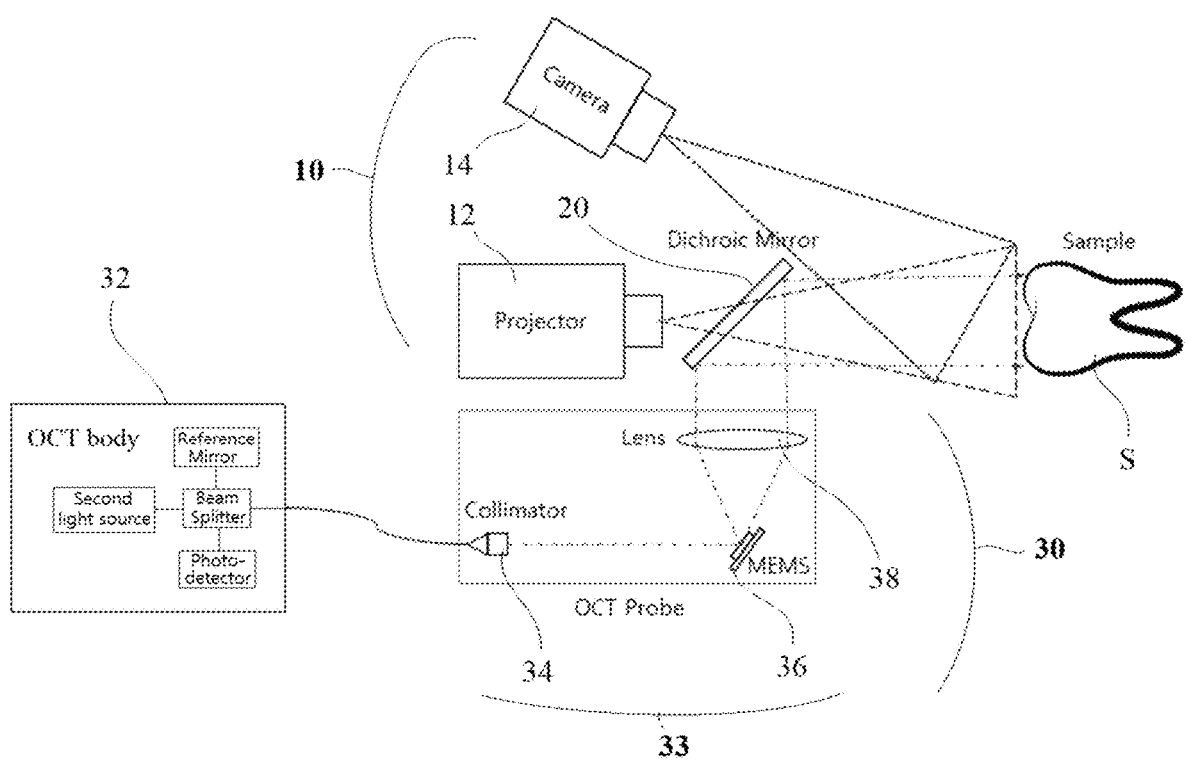
FIG. 2 is a diagram showing a tomography convergence-type oral scanner in accordance with an embodiment of the present invention.

FIG. 2 is a diagram showing the configuration of a tomography convergence-type oral scanner in accordance with an embodiment of the present invention. As shown in FIG. 2, a tomography convergence-type oral scanner in accordance with the present invention comprises an oral scanning unit 10 including a projector 12 including a first light source for generating visible light, and a camera 14 for generating image data by receiving the visible light reflected from a tooth after the visible light generated from the light source is incident on the tooth; an optical tomography scanning unit 30 including an OCT (Optical Coherence Tomography) body 32 including a second light source for generating a measurement light incident on the tooth, a beam splitter for splitting the measurement light into a reference light and a measurement light, a reference mirror that reflects the reference light, and a photodetector for detecting an interference light generated by superposition of a signal light generated by reflection of the measurement light by the tooth and the reference light reflected by the reference mirror, and an OCT scan probe 33 including a collimator lens 34 for converting the measurement light generated from the second light source into a parallel light and a MEMS (micro-electromechanical system) mirror 36 for reflecting the converted parallel light; and a dichroic mirror 20 for irradiating the tooth s with light sources in different regions by transmitting the visible light generated by the scanning unit 10 and reflecting the parallel light reflected by the MEMS mirror 36 of the optical tomography scanning unit 30.

The projector included in the oral scanning unit 10 includes the first light source for generating visible light, and in more detail, the first light source uses visible light of 400 to 700 nm. The camera further includes a sensor for receiving the visible light reflected by the tooth.

Specifically, the oral scanning unit 10 may output the visible light generated by the first light source, the visible light outputted may pass through the dichroic mirror 20 and then illuminate the inside of the oral cavity through the light irradiated from the outside along the optical path, and the light reflected from the inside of the oral cavity may reach the camera 14 along the optical path again, thereby acquiring surface shape data of the tooth in the oral cavity. At this time, the two-dimensional image of the tooth surface shape detected may be converted into a three-dimensional image by using triangulation. Specifically, by using a triangulation-based technique in the area formed by irradiating visible light to the tooth and the field of view (FOV) area of the camera 14, the surface shape of the tooth in the oral cavity may be scanned and obtained as image data.

The optical tomography scanning unit 30 in accordance with the present invention uses a non-invasive imaging technique of scanning the shape of the inside of an object by using the coherence of light and capturing an internal tomography image of a living tissue (structure) at a high resolution in the sub-micron unit.

In the optical tomography scanning unit 30, the second light source uses a light source having a wavelength different from that of the first light source (visible light) used in the oral scanning unit 10. The second light source generates a measurement light incident on the tooth s, and the measurement light is usually a broadband low-coherence light having a short coherence distance and uses, for example, near-infrared light having a wavelength of 750 nm to 1500 nm. The beam splitter divides the measurement light into a reference light and a measurement light, irradiates the reference mirror with the reference light, and passes the measurement light to a tooth to be measured. The reference light is reflected by the reference mirror and is passed back to the beam splitter. The reference light passed is superimposed with the signal light to be described below to generate an interference light.

The divided measurement light is passed to the collimator 34. The collimator 34 receives the measurement light emitted from the beam splitter and converts it into parallel light. Since the measurement light is close to a point light source, the measurement light is converted into parallel light of a certain size. The parallel light emitted from the collimator 34 is passed to the MEMS mirror 36. The MEMS mirror 36 is a device capable of changing an optical path, and can acquire a three-dimensional image of an object to be measured since one mirror rotates in two axes, specifically, the x-axis and the y-axis. As the two axes are not separated in the case of the MEMS mirror, a three-dimensional tomography image of high-resolution can be obtained without image distortion due to the refraction of light. Accordingly, the parallel light emitted from the collimator 34 is rotated in two axes (x-axis and y-axis) by the MEMS mirror to change the optical path. The light emitted from the MEMS mirror 36 is condensed by the focusing lens 38 and passed to the dichroic mirror 20. The focusing lens 38 is located between the MEMS mirror 36 and the dichroic mirror 20.

The dichroic mirror 20 may selectively transmit or reflect depending on a wavelength. Specifically, the dichroic mirror in accordance with the present invention transmits a light source in the visible region and reflects a light source having a near-infrared wavelength. Since the optical paths are not the same because light sources of different regions are usually used, there is difficulty in obtaining desired image data as the ranges of the objects to be measured do not overlap.

The tomography convergence-type oral scanner in accordance with the present invention may use the dichroic mirror to reflect wavelengths in a specific region (e.g., a second light source including near-infrared rays) of a place that is not included in the field of view (FOV) region of the camera 14, to superimpose regions of interest (ROI) to be measured, and to obtain image data of an object to be measured. Specifically, the dichroic mirror used in the tomography convergence-type oral scanner may transmit the visible light generated by the first light source of the scanning unit 10, reflect the near-infrared light generated by the second light source of the optical tomography unit 30, and superimpose the optical paths of the light sources of different regions, thereby being able to obtain the external surface shape and internal tomography image data of the tooth s to be measured. The image data may be in the form of videos, photos, or the like.

The measurement light reflected by the dichroic mirror 20 is reflected by the tooth to generate a signal light, the generated signal light reaches the OCT body 32 along the optical path again, and at this time, the signal light is superimposed with the reference light reflected by the reference mirror to generate an interference light and it is converted into an electrical signal by a photodetector that detects the interference light generated. The OCT body 32 further includes an image signal processor, and transmits the electrical signal converted by the photodetector to the image signal processor to convert it into a digital signal, and processes the digital signal to generate image data for the tooth s.

Figure 3:
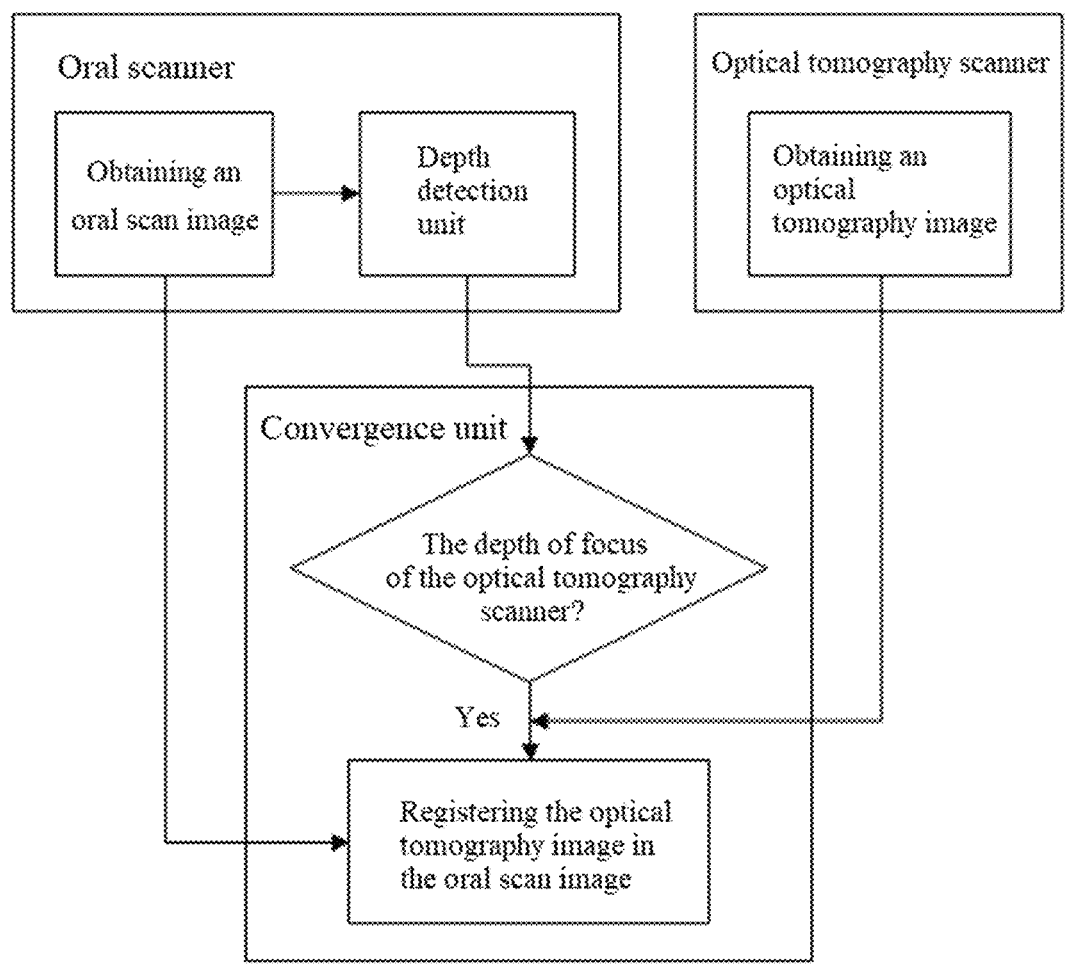
FIG. 3 is a flowchart for illustrating the operation of a tomography convergence-type oral scanner in accordance with an embodiment of the present invention.

FIG. 3 is a flowchart for illustrating the operation of an oral scanner in accordance with an embodiment of the present invention. As shown in FIG. 3 below, light sources of different regions generated by the scanning unit and the optical tomography scanning unit superimpose regions of interest (ROI), photograph the range to be measured, and obtain the external surface shape and internal tomography image data of the tooth s, respectively. The depth of focus of the optical tomography scanner is checked based on the depth information that can be obtained from the image data of the external surface shape obtained by the scanning unit. The depth of focus refers to a permissible range in which image fog or blur cannot be distinguished within a range of a certain distance before and after the object to be measured when an image plane is created by focusing on the object to be measured. Only when the depth of the optical tomography unit is the depth of focus based on the depth information obtained by the oral scanning unit, the internal tomography image data of the tooth obtained by the optical tomography unit is registered. This makes it possible to solve problems such as deviation of the depth that may occur at a low depth of the optical tomography unit, inversion of the phase of the image data in the frequency domain, and the like.

The tomography convergence-type oral scanner is to scan and photograph the intraoral tissue structure, and can scan and photograph at least part of either one of the maxilla or the mandible, for example, can simultaneously scan at least two or more teeth along the direction of the dentition, and in particular, may be possible to scan the entire dentition while minimizing changes in angle and position in the oral cavity via at least one optical system that is movable inside an extension. Common techniques may be widely applied to a structure for the movement of such an optical system. In addition, the tomography convergence-type oral scanner in accordance with the present invention is not restrictively applied to teeth, but for example, can also obtain the surface shape and internal tomography image data of the gum and the like.

The tomography convergence-type oral scanner in accordance with the present invention can obtain the external surface shape and internal tomography image data of a tooth by superimposing the optical path on the tooth to be measured by using a dichroic mirror as light sources of different regions are used. This makes it possible to further obtain partial tomography information in the shape information of the entire tooth, and thus, to further check tomography image data related to periodontal diseases such as subgingival margin acquisition and periodontitis, dental caries, cracks, biofilm etc.

Although the present invention has been described with reference to the exemplary embodiments above, the present invention is not limited to the embodiments described above. The scope of the claims that follow should be construed to encompass all modifications, and equivalent constructions and functions of the exemplary embodiments.

What is claimed is:

1. A tomography convergence-type oral scanner comprising:
   an oral scanning unit comprising a projector including a first light source for generating visible light, and a camera for generating image data by receiving the visible light reflected from a tooth after the visible light generated from the light source is incident on the tooth;
   an optical tomography scanning unit comprising an optical coherence tomography (OCT) body including a second light source that has a different wavelength from the first light source and generates a measurement light incident on the tooth, a beam splitter for splitting the measurement light into a reference light and a measurement light, a reference mirror that reflects the reference light, and a photodetector for detecting an interference light generated by superposition of a signal light generated by reflection of the measurement light by the tooth and the reference light reflected by the reference mirror, and an OCT scan probe including a collimator for converting the measurement light divided by the beam splitter into a parallel light and a MEMS mirror for reflecting the converted parallel light; and
   a dichroic mirror for transmitting the visible light generated by the oral scanning unit and reflecting the parallel light reflected by the MEMS mirror of the optical tomography scanning unit, thereby irradiating a tooth to be measured,
   wherein the second light source is near-infrared light of 750 to 1500 nm,
   wherein the dichroic mirror transmits the first light source that generates visible light and reflects the second light source having a wavelength different from that of the first light source, thereby superimposing optical paths of the light sources of different regions,
   wherein the oral scanning unit obtains image data of an external surface shape of the tooth, and the optical tomography scanning unit obtains internal tomography image data of the tooth, and
   wherein a depth information is obtained from the image data of the external surface shape obtained by the oral scanning unit, a depth of focus of the optical tomography scanning unit is determined on the basis of the depth information, and only when a depth of the optical tomography scanning unit is within the depth of focus, the internal tomography image data of the tooth obtained by the optical tomography scanning unit is registered.

2. The tomography convergence-type oral scanner of claim 1, wherein the MEMS mirror rotates in the x-axis and y-axis to change an optical path.

3. The tomography convergence-type oral scanner of claim 1, wherein the OCT scan probe further comprises a focusing lens that is located between the MEMS mirror of the OCT scan probe and the dichroic mirror and that condenses the light reflected by the MEMS mirror and passes it to the dichroic mirror.

* * * * *